United States Patent
Krätschmer et al.

(10) Patent No.: US 10,520,428 B2
(45) Date of Patent: Dec. 31, 2019

(54) OPTICAL SYSTEM

(71) Applicant: Endress+Hauser Conducta GmbH+Co. KG, Gerlingen (DE)

(72) Inventors: Thilo Krätschmer, Gerlingen (DE); Frank Müller, Stuttgart (DE); Alejandro Vaca-Torres, Steinheim (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 16/031,278

(22) Filed: Jul. 10, 2018

(65) Prior Publication Data

US 2019/0017926 A1  Jan. 17, 2019

(30) Foreign Application Priority Data

Jul. 12, 2017 (DE) .................. 10 2017 115 660

(51) Int. Cl.
  *G01J 3/28* (2006.01)
  *G01N 21/31* (2006.01)
  *G02B 6/42* (2006.01)

(52) U.S. Cl.
  CPC .......... *G01N 21/31* (2013.01); *G02B 6/4204* (2013.01); *G02B 6/4298* (2013.01)

(58) Field of Classification Search
  CPC .... G01J 3/02; G01J 3/28; G01J 3/2803; G01J 3/10; G01J 3/2823
  USPC ....................................................... 356/326
  See application file for complete search history.

(56) References Cited

U.S. PATENT DOCUMENTS

| | | | |
|---|---|---|---|
| 4,966,462 A | 10/1990 | Novick | |
| 5,517,314 A | 5/1996 | Wallin | |
| 6,010,665 A | 1/2000 | Dosoretz et al. | |
| 2004/0125459 A1* | 7/2004 | Tanitsu | G02B 3/0056 359/619 |
| 2005/0046850 A1* | 3/2005 | Chow | G01B 11/0625 356/430 |
| 2009/0103081 A1* | 4/2009 | Whelan | G01J 3/28 356/243.1 |
| 2011/0261359 A1 | 10/2011 | Inada et al. | |
| 2013/0250307 A1* | 9/2013 | Tamiya | G01B 9/02015 356/498 |
| 2014/0022546 A1* | 1/2014 | Nagai | G01J 3/021 356/326 |

(Continued)

FOREIGN PATENT DOCUMENTS

DE  102015116386 A1  3/2017

OTHER PUBLICATIONS

Search Report for German Patent Application No. 10 2017 115 660.7, German Patent Office, dated Mar. 6, 2018, 7 pp.

*Primary Examiner* — Md M Rahman
(74) *Attorney, Agent, or Firm* — Mark A. Logan; PatServe

(57) ABSTRACT

The invention relates to an optical system for measuring the absorption of light in a medium, comprising at least one light source for sending light and at least one optical detector, which receives the light and converts it into an electrical signal. The system is characterized in that the system comprises at least one light guide, wherein, in the region of the light source, light is coupled as reference light into the light guide, wherein the light guide is guided, at least in sections, past the medium, and wherein the light guide guides the reference light onto the detector.

9 Claims, 2 Drawing Sheets

(56) References Cited

U.S. PATENT DOCUMENTS

2015/0062586 A1* 3/2015 Zhu .................... G01J 3/45
                                                      356/453
2015/0276484 A1* 10/2015 Matsuzawa ............ G01J 3/443
                                                      356/316

* cited by examiner

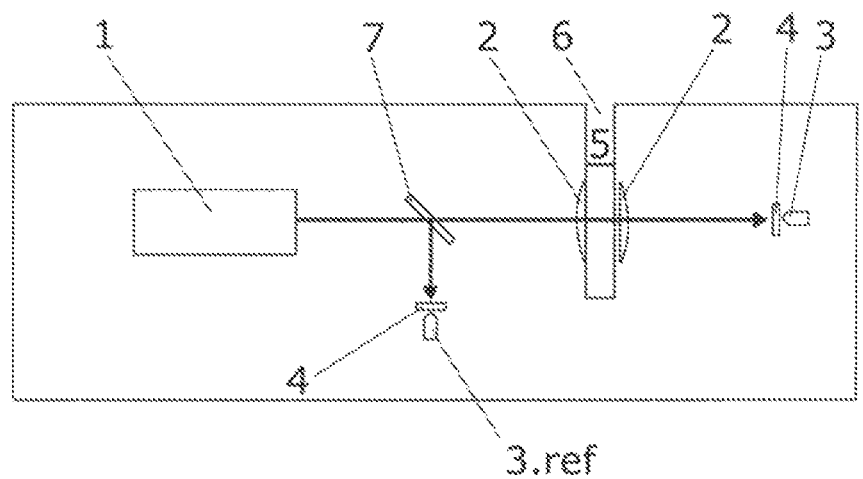

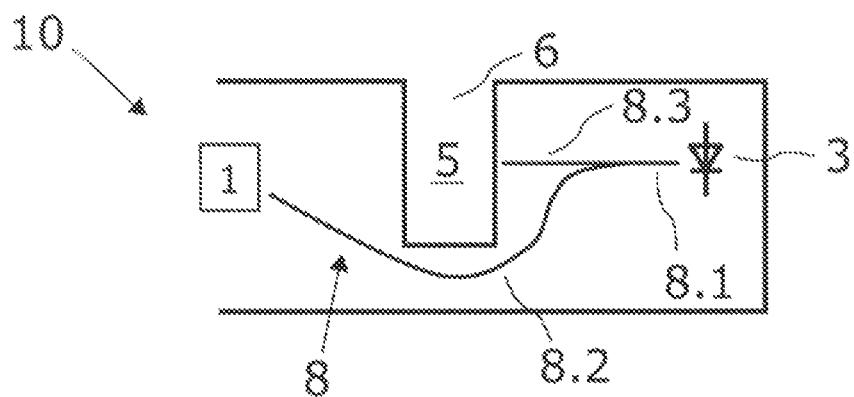
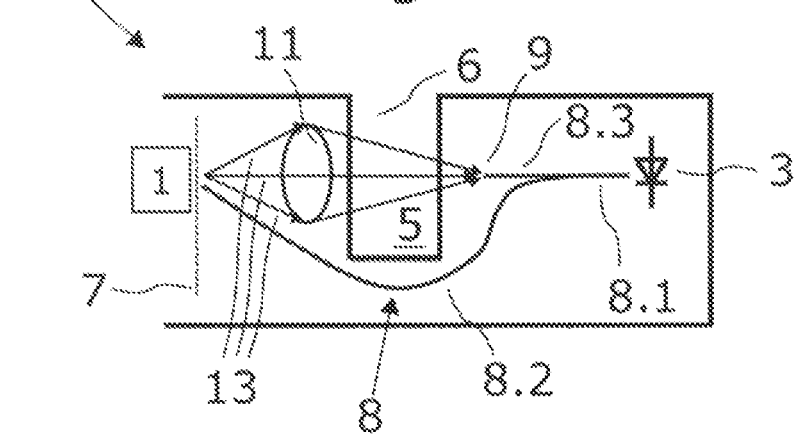
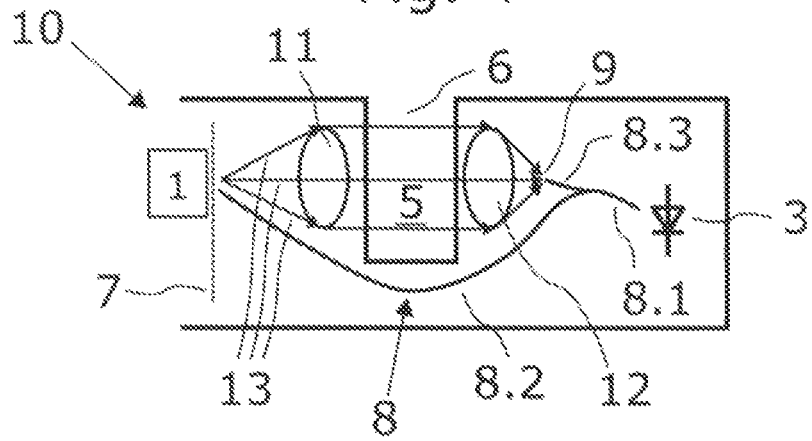

OPTICAL SYSTEM

CROSS-REFERENCE TO RELATED APPLICATION

The present application is related to and claims the priority benefit of German Patent Application No. 10 2017 115 660.7, filed on Jul. 12, 2017, the entire contents of which are incorporated herein by reference.

TECHNICAL FIELD

The invention relates to an optical system for measuring the absorption of light in a medium.

BACKGROUND

"Absorption" generally refers to the absorption of a wave (electromagnetic waves, sound waves, as well as light) in an absorbent material. During absorption, transmission is dampened by the material. Absorption measurement in process automation is, for example, used to determine nitrate or to measure the spectral absorption coefficient (SAC), e.g., in order to determine the organic load/charge in sewage treatment plants or in drinking water.

FIG. 1 shows the basic measurement principle according to the prior art. The light of a light source 1, e.g., a pulsed flash lamp, irradiates the measurement section 5. Medium 5 is located in gap 6, wherein the measurement light radiated into said medium is absorbed by the determining process variable. The measurement section comprises optical windows 2, which, where applicable, also comprise lenses. A beam splitter 7 finally guides the light onto the two detectors 3 for measurement light or 3.ref for reference light. A filter 4, which allows only light of the measurement wavelength or only light of the reference wavelength to pass through in the case of the detector 3, 3.ref, is respectively mounted, where applicable, in front of the two detectors 3, 3.ref. The beam splitter 7 may also be arranged after the gap 6.

The above shall be explained below by way of example on the basis of a nitrate measurement. Nitrations absorb UV light in the range of approximately 190 nm to 230 nm. Nitritions have a similar absorption in the same range. In the gap 6, the nitrations and nitritions absorb UV light in the range of the measurement wavelength 214 nm in proportion to their concentration.

If signs of aging or temperature influences of a light source do not have any influence on the measured value of an optical probe, the light source must be monitored. In many applications, this is achieved by a second detector system (photodiode or spectrometer) directly at the light source (see FIG. 1). Any existing measurement and reference filters are in this case designed to be identical (same wavelength). If, however, this method cannot be used, either because there is no space for a second detector system in the probe or because a second detector system is too expensive, and, if a regular calibration in a zero solution also cannot be performed, the light of the light source must be guided around the measurement cuvette onto the measurement detector or the measurement spectrometer.

For process sensors that are to remain in the process for a long period of time, and thus also during the necessary reference measurements of the light source, the light of the light source therefore must be guided within the sensor along an optical path that is different from the measurement beam path past the measurement section onto the detector system. Since this reference beam cannot be located on the same optical axis of the measurement beam, various optical free-beam components are required in order to guide the reference beam past the measurement section and, on the receiving side, once again onto the detector system. These optical free-beam components can, for example, include lenses, beam splitters, and mirrors (see, for example, DE 100 84 057 B4). In order to generate a stable reference signal, it is also necessary to align these components correctly and robustly in relation to each other.

The necessary optical free-beam components occupy a lot of space, which may be an obstacle in process sensors that become smaller and smaller. Both the optical free-beam components and the production costs for their alignment are costly. Optical free-beam components can, moreover, be soiled, e.g., by humidity or by accumulation of evaporated materials.

SUMMARY

The invention is based upon the aim of easily, cost-effectively, and robustly monitoring the light source of an optical system that functions, in particular, in accordance with the absorption principle.

The aim is achieved by an optical system comprising at least one light source for sending light and at least one optical detector that receives the light and converts it into an electrical signal. The system is characterized in that the system comprises at least one light guide, wherein, in the region of the light source, light is coupled as reference light into the light guide, wherein the light guide is guided, at least in sections, past the medium, and wherein the light guide guides the reference light onto the detector.

A cost-efficient structure that is robust with respect to mechanical loads thus results. By using a light guide, a flexible structure results, e.g., the detector can thus be freely placed. Moreover, less optical components are required in comparison to the aforementioned prior art. For this reason, but also in principle, a more space-saving structure than in the prior art results. If less or no optical components are used, the system is less prone to soiling and positioning inaccuracies.

The term, "light," in this case refers not only to visible light, but also to invisible infrared light and ultraviolet radiation.

"Light guide" refers to transparent components such as individual fibers, fiber bundles, tubes, or rods that transport light over short or long distances. Light guidance is in this case achieved by reflection on the boundary surface of the light guide either through total reflection as a result of a lower refraction index of the medium surrounding the light guide or through mirroring of the boundary surface.

In one embodiment, light is radiated by the light source as measurement light in the direction of the medium and guided by the light guide onto the detector after absorption in the medium.

In one embodiment, the system comprises a light selector, which switches light of the light source between measurement light and reference light.

In one embodiment, the light selector changes the optical beam path. To this end, the light selector comprises a foldable mirror, or one end of the light guide is movable so that either the measurement light or the reference light impinges on the detector. Other components for changing the beam path are also, basically, possible.

In one embodiment, the light selector leaves the optical beam path unchanged and instead blocks either the measurement light or the reference light, but not the respective other light. In one embodiment, the light selector is a moving aperture.

In one embodiment, the light guide is designed in the shape of a Y, wherein the single branch leads in the direction of the detector, and the two other branches guide reference light or measurement light. Since the same light guide is used for measurement light and reference light, potential aging effects of the light guide are also compensated for. This is not possible in the described prior art by using several free-beam components.

In one embodiment, the system comprises at least one first light guide for measurement light and at least one second light guide for reference light. In this case, the first and second light guides differ as to type, diameter, material, and/or number of fibers. As a result, the spectral transmission range can be expanded in comparison to the prior art. The embodiment proposed above can also be used in the Y waveguide. The individual branches then have different light guides, as described.

In one embodiment, in which the light guide is designed in the shape of a Y, the light selector comprises a fiber switch, which switches between measurement and reference light, i.e., changes between measurement section and reference section.

In one embodiment, the system comprises exactly one light guide.

The medium divides the system into a light-source side and a detector side. In one embodiment, the system comprises, in the region of the light source, at least one optical component comprising at least one lens—in particular, a biconvex lens—for guiding the measurement light into the direction of the medium. As a result, light can be efficiently and easily guided through the medium into the direction of the detector.

In one embodiment, the optical component focuses the measurement light onto the light guide on the detector side.

In one embodiment, the system comprises, on the detector side, at least one optical component, comprising at least one lens, which focuses measurement light absorbed by the medium onto the light guide.

The system comprises an optical axis, which is essentially defined by the light source and the end of the light guide for measurement light on the detector side. In one embodiment, the detector is arranged apart from this optical axis of the system.

In one embodiment, the detector is designed as a spectrometer, so that the spectrum of the light impinging on the detector can be displayed.

BRIEF DESCRIPTION OF THE DRAWINGS

This will be explained in more detail with reference to the following figures. Shown are:
FIG. 1 shows the basic measurement principle according to the prior art;
FIG. 2 shows an embodiment of the system claimed;
FIG. 3 shows another embodiment of the system claimed; and
FIG. 4 shows another embodiment of the system claimed.

DETAILED DESCRIPTION

In the figures, the same features are identified with the same reference symbols.

The claimed optical system, in its entirety, has reference symbol 10. Any necessary optical windows, as shown in FIG. 1, are not drawn in FIGS. 2-4, for reasons of clarity.

The optical system 10 comprises at least one light source 1 for sending light 13. The light source is a broadband light source and designed, for example, as a Xenon flash lamp. Alternatively, an array of LED's, for example, is used. A possible wavelength range includes the range of 1,900-1,000 nm. The system 10 comprises a detector 3. The medium to be measured has reference symbol 5. A gap 6, e.g., a cuvette, is located between light source 1 and detector 3. The detector 3 is designed as a spectrometer, so that the spectrum of the light impinging on the detector 3 can be displayed, e.g., in a connected measurement transducer.

In the embodiment of FIG. 2, light of light source 1, in the region of the light source, is coupled into a light guide 8. The light guide 8 is constructed in the shape of a Y with branches 8.1, 8.2, 8.3. The single branch 8.1 points in the direction of detector 3 or directly leads into detector 3. In one embodiment, both branches can also be led directly into detector 3. In this case, a common ferrule is, for example, used. Both branches thus directly lead into detector 3. This can also be carried out using a plurality of light guides.

A light selector 7 (not shown in FIG. 2, but see FIGS. 3-4) for switching between a measurement section and a reference section is used. A first single branch 8.3 of the light guide 8 is used for the measurement section ("measurement light"); a second branch 8.2 is used for the reference section ("reference light"). The light selector 7 is a moving aperture, so that either measurement light or reference light is blocked. The actual beam path remains unchanged by the light selector 7. In one embodiment, the light selector 7 is mounted as an optical switch at the branching point of the Y waveguide.

The light guide 8 is guided past medium 5 in sections; more precisely, at least one branch—in this case, branch 8.2—is guided past said medium. The reference section with the reference light thus leads past medium 5.

In one possible embodiment (see FIG. 3), the light 13 of light source 1 is focused onto the opening of light guide 8 using optics comprising at least one lens 11, which is located either between light source 1 and cuvette 6 or between cuvette 6 and branch 8.3 of light guide 8. This takes place at the point of concentration 9. The lens 11 is designed as a biconvex lens. FIG. 3 shows the first case. The reference section is guided around the cuvette 6; the measurement section, naturally, passes through the medium 5.

In one embodiment (see FIG. 4), the system 10 comprises first optics comprising at least one first lens 11 and second optics comprising at least one second lens 12. The first lens 11 parallelizes impinging light 13, which is guided through the medium 5. The second lens 12 focuses the light onto the opening of light guide 8—more precisely, onto branch 8.3. This takes place at the point of concentration 9. The reference section is guided around the cuvette 6; the measurement section, naturally, passes through the medium 5.

Detector 3 can be arranged such that it is not located on the optical axis (see FIG. 4). The optical axis is defined by the light source 1 and the end of the branch of the light guide 3 for measurement light, i.e., the branch with reference symbol 8.3 in this case.

The light guide 3 comprises transparent components, such as fibers, tubes, or rods, that transport light over short or long distances. In this case, the light guide 3 comprises one or more fibers. By using several fibers of one type, as well as by using different fiber diameters, different materials, or different types, the signal strength for the measurement and reference light can be influenced independently of each other. To this end, no additional optical components (aperture, etc.) are needed.

By suitable selection of the optical fibers of the light guide and, where applicable, also by using several fiber types, a very broad spectral range of application can be covered. For example, UV, VIS, NIR, and MIR fibers can be integrated into an optical multi-type fiber.

What is claimed is:

1. An optical system for measuring the absorption of light in a medium, comprising:
    a cuvette embodied to contain the medium;
    a light source for sending light, wherein the light source is configured to radiate light as measurement light into the medium in the cuvette;
    an optical detector embodied to receive the light and to convert the received light into an electrical signal;
    a first light guide, wherein, in the region of the light source, the first light guide is embodied to couple light as reference light into the first light guide and to guide the reference light past the cuvette and onto the optical detector; and
    a light selector configured to switch the light of the light source between measurement light and reference light, wherein the light selector is disposed between the light source and the cuvette and also between the light source and the first light guide,
    wherein the first light guide is further embodied to guide the measurement light onto the detector after absorption in the medium in the cuvette.

2. The optical system according to one of claim 1, wherein the first light guide is designed in the shape of a Y, and wherein a first branch leads in the direction of the optical detector, a second branch guides the reference light, and a third branch guides the measurement light.

3. The optical system according to claim 1, which comprises exactly one light guide.

4. The optical system according to claim 1, further comprising:
    a second light guide for reference light, wherein the first light guide and the second light guide differ as to type, diameter, material, and/or number of fibers.

5. The optical system according to one of claim 1, further comprising:
    a first optical component including a biconvex lens disposed in the region of the light source and configured to guide the measurement light into the direction of medium.

6. The optical system according to claim 5, wherein the first optical component is configured to focus the measurement light onto the first light guide on the optical detector side.

7. The optical system according to claim 5, further comprising:
    on the optical detector side, a second optical component including at least one lens and configured to focus absorbed measurement light onto the first light guide.

8. The optical system according to claim 1, wherein the optical detector is arranged apart from an optical axis of the system.

9. The optical system according to claim 1, wherein the optical detector is designed as a spectrometer such that a spectrum of the light impinging on the optical detector is displayed.

* * * * *